US008987523B2

(12) United States Patent
Kreickmann et al.

(10) Patent No.: US 8,987,523 B2
(45) Date of Patent: Mar. 24, 2015

(54) METHOD FOR OBTAINING DITRIMETHYLOLPROPANE AND TRIMETHYLOLPROPANE-ENRICHED PRODUCT STREAMS FROM THE SIDE-STREAMS IN TRIMETHYLOLPROPANE PRODUCTION

(75) Inventors: Thorsten Kreickmann, Oberhausen (DE); Guido D. Frey, Riedstadt (DE); Norman Nowotny, Essen (DE); Heinz Strutz, Moers (DE)

(73) Assignee: Oxea GmbH, Oberhausen (DE)

( * ) Notice: Subject to any disclaimer, the term of this patent is extended or adjusted under 35 U.S.C. 154(b) by 280 days.

(21) Appl. No.: 13/810,723

(22) PCT Filed: Jul. 28, 2011

(86) PCT No.: PCT/EP2011/003788
§ 371 (c)(1),
(2), (4) Date: Jan. 17, 2013

(87) PCT Pub. No.: WO2012/019714
PCT Pub. Date: Feb. 16, 2012

(65) Prior Publication Data
US 2013/0131391 A1 May 23, 2013

(30) Foreign Application Priority Data
Aug. 11, 2010 (DE) .......................... 10 2010 033 844

(51) Int. Cl.
| C07C 41/34 | (2006.01) |
| C07C 29/74 | (2006.01) |
| C07C 29/10 | (2006.01) |
| C07C 29/80 | (2006.01) |
| C07C 29/90 | (2006.01) |
| C07C 41/42 | (2006.01) |
| C07C 41/44 | (2006.01) |

(52) U.S. Cl.
CPC .................. *C07C 29/74* (2013.01); *C07C 29/10* (2013.01); *C07C 29/80* (2013.01); *C07C 29/90* (2013.01); *C07C 41/42* (2013.01); *C07C 41/44* (2013.01); *C07C 41/34* (2013.01)

USPC .......................................... 568/680; 568/854

(58) Field of Classification Search
CPC ........ C07C 41/44; C07C 41/42; C07C 41/34; C07C 29/90; C07C 29/80; C07C 29/74; C07C 29/10
USPC .................................................. 568/680, 854
See application file for complete search history.

(56) References Cited

U.S. PATENT DOCUMENTS

| 3,962,347 A | 6/1976 | Herz |
| 5,603,835 A | 2/1997 | Cheung et al. |
| 5,948,943 A | 9/1999 | Supplee et al. |
| 6,586,641 B2 * | 7/2003 | Dernbach et al. ............. 568/853 |
| 2004/0254405 A1 | 12/2004 | Kuzuhara et al. |

FOREIGN PATENT DOCUMENTS

| DE | 2058518 | 6/1971 |
| DE | 19840276 A1 | 3/2000 |
| DE | 010058303 A1 * | 5/2002 ............. C07C 29/80 |
| DE | 10 2008 038021 A1 | 2/2010 |
| WO | 9717313 A1 | 5/1997 |
| WO | 2004013074 A1 | 2/2004 |

OTHER PUBLICATIONS

International Search Report, Sep. 30, 2011.
International Preliminary Report on Patentability, Feb. 12, 2013.

* cited by examiner

*Primary Examiner* — Rosalynd Keys
(74) *Attorney, Agent, or Firm* — Michael W. Ferrell

(57) ABSTRACT

The present invention relates to a process for obtaining ditrimethylolpropane and trimethylolpropane-enriched product streams from the high-boiling fractions and residues which are obtained in the distillative purification of trimethylolpropane, wherein an aqueous solution of these fractions and residues is catalytically hydrogenated in the presence of an acidic compound and, after removing solids, contacted both with basic and with acidic ion exchangers. A trimethylolpropane-enriched product stream can be distilled out of the aqueous eluate obtained, leaving ditrimethylolpropane as the distillation residue.

15 Claims, No Drawings

METHOD FOR OBTAINING DITRIMETHYLOLPROPANE AND TRIMETHYLOLPROPANE-ENRICHED PRODUCT STREAMS FROM THE SIDE-STREAMS IN TRIMETHYLOLPROPANE PRODUCTION

CLAIM FOR PRIORITY

This application is a national phase application of PCT/EP2011/003788 FILED Jul. 28, 2011 which was based on application DE 10 2010 033 844 filed Aug. 11, 2010. The priorities of PCT/EP2011/003788 and DE 10 2010 033 844 are hereby claimed and their disclosures incorporated herein by reference.

TECHNICAL FIELD

The present invention relates to a process for obtaining ditrimethylolpropane and trimethylolpropane-enriched product streams from the secondary streams of trimethylolpropane preparation.

BACKGROUND

Trimethylolpropane is a trihydric alcohol which is of significance for the production of coating materials, polyurethanes and polyesters, for example of alkyd resins. Trimethylolpropane is produced industrially by condensation reaction of n-butyraldehyde with formaldehyde according to different variants.

In what is called the hydrogenation process, at least two moles of formaldehyde are added onto one mole of n-butyraldehyde in the presence of a catalytic amount of a tertiary amine via the monomethylolbutyraldehyde intermediate to initially give dimethylolbutyraldehyde, which is then converted to trimethylolpropane in a hydrogenation step. According to the process described in WO98/28253 A1, formaldehyde is used with an up to eight-fold molar excess. The reaction mixture obtained from the aldol addition step is worked up either by distillation or by phase separation. In the distillative workup, unconverted or partly converted starting compounds are drawn off as volatile components and recycled into the reaction stage, while the bottom product is converted further. If, instead of the distillative workup, the reaction mixture is separated in a phase separator into the aqueous and organic phases, the organic phase is returned to the aldol addition and the aqueous phase is processed further. There follows a catalytic and/or thermal treatment in order to convert monomethylolbutyraldehyde to dimethylolbutyraldehyde. By-products formed are removed by distillation and the bottom product of this distillation is subsequently catalytically hydrogenated to obtain trimethylolpropane. The crude trimethylol-propane obtained is subsequently subjected to a purifying distillation. After removal of low and medium boilers, purified trimethylolpropane is obtained as an intermediate fraction, while higher-boiling condensation products within which trimethylolpropane equivalents are bound are obtained as the tailings or bottom fraction.

In addition to the hydrogenation process, trimethylol-propane is also prepared industrially by what is known as the Cannizzaro reaction. In a first reaction stage, n-butyraldehyde and formaldehyde are reacted with addition of stoichiometric amounts of a base to give dimethylolbutyraldehyde, which is subsequently reduced with excess formaldehyde to give trimethylolpropane, while one equivalent of formate is formed simultaneously. Typically, the base used is an aqueous solution of an alkali metal or alkaline earth metal compound, for example sodium hydroxide, potassium hydroxide or calcium hydroxide. Since one equivalent of alkali metal or alkaline earth metal formate is obtained as a coproduct in the Cannizzaro process, the economic viability of this process variant also depends on the marketing opportunities for this coproduct. The workup of the aqueous reaction solution obtained, which comprises trimethylolpropane, alkali metal or alkaline earth metal formate and excess base, is effected generally by extraction. After neutralization of the excess base, the aqueous solution is extracted with an organic solvent, for example with ethyl acetate. The organic phase is separated from the aqueous phase, which comprises the alkali metal or alkaline earth metal formates in dissolved form, and, after removal of the extractant, trimethylolpropane is obtained by distillation. The resulting trimethylolpropane can be subjected to further purification processes. According to U.S. Pat. No. 5,603,835, an aqueous solution is first prepared from resulting trimethylolpropane, and is extracted once again with an organic solvent, for example with methyl tert-butyl ether. Trimethylolpropane is obtained from the resulting aqueous solution with an improved colour number of less than 100 APHA units.

According to the process known from U.S. Pat. No. 5,948,943, the aqueous, crude reaction solution obtained after the Cannizzaro reaction is treated with a suitable organic solvent at such a temperature that only one liquid phase leaves the extraction vessel. In the subsequent cooling outside the extraction vessel, the aqueous phase separates from the organic phase, and trimethylolpropane can be isolated from the aqueous phase with a colour number of less than 100 APHA.

It is likewise known that the Cannizzaro reaction can be performed with an organic base, for example with a tertiary amine. According to the procedure known from WO97/17313 A1, formaldehyde is prepared with n-butyraldehyde in the presence of stoichiometric amounts of a tertiary amine, forming one equivalent of ammonium formate. Subsequently, water, excess tertiary amine and excess formaldehyde are removed from the crude mixture, and the remaining mixture is heated. This dissociates the ammonium formates to the tertiary amine and formic acid, and the tertiary amine and further volatile constituents are removed, resulting in the formation of trimethylolpropane formate. The tertiary amine removed is either recycled into the Cannizzaro stage or used as a catalyst for the transesterification of the trimethylolpropane formate in a downstream reaction with an added lower aliphatic alcohol. The trimethylolpropane released is subsequently isolated from the crude product.

Irrespective of whether the preparation of trimethylol-propane is effected by the hydrogenation process using catalytic amounts of a tertiary amine, by the Cannizzaro process with molar amounts of a tertiary amine and subsequent transesterification of the trimethylolpropane formate formed, or by the Cannizzaro process with molar amounts of alkali metal or alkaline earth metal hydroxides and the extractive removal thereof, the crude trimethylolpropane obtained is subjected to a single or multiple distillative purification, which is effected under reduced pressure due to the high boiling point. According to DE 100 58 303 A1, the distillative workup of the trimethylolpropane is combined with an ion exchanger treatment, in which case either the aldolization output or the hydrogenation output is contacted with a strongly basic ion exchanger before the distillative workup.

Distillative workup gives rise to high-boiling fractions with a higher boiling point compared to trimethylolpropane, or residues in which derivatives of trimethylolpropane are present and have formed therefrom by reaction with, for example, methanol, formaldehyde or else with a further molecule of trimethylolpropane in the upstream reactions. Among these derivatives, particularly formaldehyde-containing acetals are represented, which are characterized by the structural element —O—CH$_2$—O— and can also be regarded as formals. Among the formals, the following linear and cyclic formals of trimethylolpropane can be described structurally:

Monocyclic formal of trimethylolpropane:

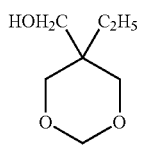
Formula I

Linear bistrimethylolpropane formal:

[C$_2$H$_5$C(CH$_2$OH)$_2$CH$_2$O]$_2$CH$_2$      Formula II

Methyl (monolinear) formal of trimethylolpropane:

C$_2$H$_5$C(CH$_2$OH)$_2$CH$_2$OCH$_2$OCH$_3$      Formula III

Methyl (bislinear) formal of trimethylolpropane:

C$_2$H$_5$C(CH$_2$OH)$_2$CH$_2$OCH$_2$OCH$_2$OCH$_3$      Formula IV

In this context, the monocyclic formal of trimethylol-propane (I) boils at a lower temperature than trimethylolpropane itself. The methanol-derived formals (III) and (IV) have a boiling point comparable to trimethylolpropane, while the linear bistrimethylol-propane formal (formula II) is present as a high-boiling component. In addition, further linear and cyclic oxygen compounds, such as the cyclic formal of ditrimethylolpropane

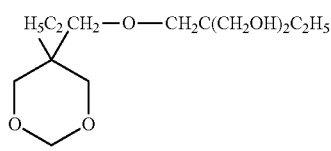
Formula V are present in the distillation residues.

Likewise present in the high-boiling fractions and residues of the distillative workup of crude trimethylolpropane are also substantial amounts of ditrimethylolpropane [C$_2$H$_5$C(CH$_2$OH)$_2$—CH$_2$—]$_2$—O and trimethylolpropane itself. Additionally present in small amounts are low-boiling components, such as methanol or 2-ethyl-1,3-propanediol.

Since the high-boiling fractions and residues of the distillative workup of trimethylolpropane include considerable amounts of derivatives in which equivalents of trimethylolpropane are chemically bound, a number of processes are proposed to dissociate especially formaldehyde-containing acetals and to release trimethylolpropane, in order in this way to improve the yield of the overall trimethylolpropane preparation process. According to WO 2004/013074 A1, the high-boiling fractions and distillation residues obtained in the trimethylolpropane preparation are treated with acid, and the water content in the reaction mixture should be 20-90% by weight. It is possible either to obtain trimethylolpropane by distillation from the acid-treated product or to recycle the treated product into the hydrogenation stage of dimethylolbutyraldehyde to give trimethylol-propane. The hydrogenating dissociation of linear or cyclic acetals in aqueous solutions in the presence of a heterogeneous hydrogenation catalyst to give the desired polyhydric alcohol is known from DE 198 40 276 A1. The process requires hydrogenation temperatures above 160° C. in order to suppress the harmful influence of formates, which may still be present particularly in the case of working by the Cannizzaro process, on the hydrogenation performance of the catalyst. The hydrogenating, catalytic dissociation can likewise be performed in the presence of an acid, for example in the presence of a lower carboxylic acid or acidic solids.

The high-boiling fractions and the residues of the distillative workup of the trimethylolpropane preparation comprise, in addition to the aforementioned formaldehyde-containing acetals, also significant amounts of ditrimethylolpropane, which is likewise of industrial significance as a valuable starting material for production of alkyd resins, plasticizers and lubricants. The prior art discloses processes for obtaining ditrimethylolpropane from these residues, and further purifying product thus obtained if required.

According to DE 2058518 A1, the ditrimethylolpropane-containing distillation residue is subjected to a steam distillation with superheated steam under reduced pressure. After removal of water, ditrimethylolpropane is obtained from the resulting aqueous distillate, and can be recrystallized if required from an organic solvent, for example acetone.

Since the distillative purification of ditrimethylol-propane is possible only with very great difficulty owing to the high boiling point, and there is also a risk of decomposition of the ditrimethylolpropane due to the high temperatures to be employed, the direct workup of the distillation residue by recrystallization to obtain ditrimethylolpropane is also described. DE 2358297 A1 considers the simple crystallization of an aqueous solution of the distillation residue, wherein the salt concentration in the aqueous solution is adjusted to a particular ratio in order to enable the precipitation of ditrimethylolpropane in sufficient purity. When trimethylolpropane is prepared by the Cannizzaro process, the salt content, for example the alkali metal formate content, in the distillation residue may already be sufficiently high to ensure the precipitation of ditrimethylolpropane crystals in a satisfactory manner after dissolution in water. It may be necessary to add a further salt to the aqueous solution, for example an alkali metal salt.

US 2004/0254405 A1 discloses a process for recrystallizing the distillation residue using organic solvents, for example acetone or methyl ethyl ketone, which requires a particular degree of observance of the crystallization temperature, the amount of solvent and the ditrimethylolpropane content in the distillation residue. The use of a mixture of a suitable solvent and water for the isolation of ditrimethylolpropane from the distillation residues of the trimethylolpropane preparation is described in DE 10 2008 038 021 A1. An organic solvent phase and a viscous residue are initially obtained, the phases are separated and the organic solvent phase is extracted with water. The water phase is isolated and solvent residues present are removed. Ditrimethylolpropane is crystallized from the remaining water phase.

The known processes for obtaining ditrimethylolpropane from high-boiling fractions and residues which have a higher boiling point than trimethylolpropane and which are obtained in the distillative workup in the course of trimethylolpropane preparation require either complex recrystallization steps or a complex steam distillation with the subsequent removal of water from the steam distillate.

There is therefore a need to obtain ditrimethylol-propane from such high-boiling fractions and residues in a very simple manner with such a purity required for the envisaged industrial applications. At the same time, trimethylolpropane still present in a physical mixture in these fractions and residues, and also derivatives present therein containing chemically bound trimethylolpropane units, should likewise be isolated as a trimethylolpropane-rich fraction which can be recycled back into the trimethylolpropane purification process, such that not only the recovery of pure ditrimethylolpropane but also the yield of trimethylol-propane over the entire preparation process can be improved. In this way, the high-boiling fractions and residues which are obtained in the distillative workup in the course of trimethylolpropane preparation can be utilized in a very economically viable manner.

SUMMARY OF INVENTION

The present invention therefore relates to a process for obtaining ditrimethylolpropane and trimethylolpropane-enriched product streams from the high-boiling fractions and residues which are obtained in the distillative purification of trimethylolpropane. It is characterized in that:
(a) these high-boiling fractions and residues are combined and water is added to produce an aqueous solution;
(b) the aqueous solution produced according to step a) is treated at a temperature of 160 to 280° C. and at a pressure of 1 to 30 MPa with hydrogen in the presence of a catalyst and of an acidic compound;
(c) the aqueous solution obtained according to step b) is removed from the catalyst and further solids, if present;
(d) the aqueous solution obtained according to step c) is treated both with basic and with acidic ion exchangers;
(e) water and low boilers present are removed from the aqueous eluate obtained according to step d); and
(f) a trimethylolpropane-enriched product stream is distilled out of the residue obtained after step e) at elevated temperature and reduced pressure, leaving ditrimethylol-propane as the distillation residue.

DETAILED DESCRIPTION

Starting materials for the process according to the invention are product streams which are obtained in the distillative purification of trimethylolpropane and have a higher boiling point than trimethylolpropane and can be referred to as high-boiling fractions. In addition to these high-boiling components which, however, are still volatile in the distillation, the remaining distillation residue is also used in the process according to the invention. These combined product streams comprise, as main components, trimethylolpropane still present in a physical mixture, generally within a range from 5 to 30% by weight, ditrimethylolpropane, generally within a range from 10 to 30% by weight, and the linear bistrimethylolpropane formal within a range from 25 to 60% by weight, based on the overall starting material. Further identified products are 2-ethyl-1,3-propanediol and the monocyclic formal of trimethylolpropane, which, due to their comparatively low boiling point, are present only in small amounts of typically up to 2% by weight. Cyclic and linear formals, including the methyl (monolinear) formal of trimethylolpropane (III), the methyl (bislinear) formal of trimethylolpropane (IV) and the cyclic formal of ditrimethylolpropane (V) form the remainder of the organic components in the mixture.

Irrespective of whether trimethylolpropane is prepared by the Cannizzaro process using alkali metal or alkaline earth metal compounds or is produced by the hydrogenation process in the presence of catalytic amounts of trialkylamines, or by the Cannizzaro process using stoichiometric amounts of trialkylamines, the high-boiling fractions and the residues which are obtained in the distillative purification of trimethylolpropane by the particular preparation process are worked up in accordance with the inventive procedure. In addition, the starting mixture may also comprise alkali metal or alkaline earth metal formates, the contents of which vary as a function of the type of process employed for the preparation of trimethylol-propane.

The high-boiling fractions which have a higher boiling point than trimethylolpropane, and the residues from the distillation of trimethylolpropane, are combined, and water is added to form an aqueous solution. In general, an aqueous solution is prepared with a content of organic components of 40 to 90% by weight, preferably of 50 to 90% by weight, especially of 50 to 80% by weight and very particularly of 60 to 80% by weight, based on the total mass. Lower contents of organic components are inappropriate due to the high water content; in the case of excessively high contents, particularly at room temperature, inhomogeneities in the aqueous solution or the precipitation of solids are to be expected. It is appropriate to prepare the aqueous solution at a temperature of more than 50° C. A temperature range for the aqueous solution of 60° C. to 80° C. should preferably be established.

The aqueous solution obtained is subsequently treated at elevated temperature and elevated pressure with hydrogen in the presence of a catalyst and of an acidic compound. The temperatures employed are in the range from 160 to 280° C., preferably 180 to 230° C., and the pressures employed are in the range from 1 to 30 MPa, preferably 6 to 20 MPa. The acidic compounds present may be protic inorganic acids, organic acids or acidic solids. Useful protic inorganic acids include phosphoric acid or sulphuric acid; useful organic acids include lower carboxylic acids such as formic acid, acetic acid, propionic acid or the isomeric butyric acids. The amount thereof is such that the aqueous solution to be subjected to the hydrogenation has a pH in the range from 1 to 5, preferably from 1 to 3. Due to the easy removability, however, preference is given to working with acidic solids as the acidic compound. Suitable solids of this kind are, for example, oxidic compounds such as acidic alumina, natural or silicatic substances such as mordenite, montmorillonite or acidic zeolites, for example those of the Y type, which are available in industrial amounts and are used industrially, for example, in the catalytic cracking of crude oils. The addition therefore is guided by the acidity thereof and, for every 100 parts by weight of aqueous solution, they are used generally in an amount of 0.5 to 2, preferably of 0.5 to 1.0, parts by weight, and the more acidic the solid the smaller the amounts used.

It is also possible to use commercially available acidic ion exchangers, for example strongly acidic ion exchangers such as Amberlyst 15, Amberlite IR 120, Amberlyst DPT-1, Dowex Marathon-C, Dowex HCR or Lewatit S 100, or weakly acidic ion exchangers such as Amberlite ICR 86 or Lewatit CNP. The addition thereof is guided by the acidity thereof, and they are generally used in an amount of 1 to 20 and preferably of 5 to 10 parts by weight, based on 100 parts by weight of aqueous solution, and the more acidic the solid the smaller the amounts used.

The catalysts used for the hydrogenation step are customary hydrogenation catalysts, preference being given to heterogeneous hydrogenation catalysts since they can be removed from the reaction mixture in a simple manner, for example by simple filtration in the case of suspension hydrogenation. In the case of fixed bed catalysts too, for example in trickle or liquid phase mode, the reaction mixture can be separated easily from the hydrogenation catalyst.

Typical hydrogenation catalysts comprise, as active components, a noble metal from the group of Ru, Rh, Pd and Pt or a transition metal from the group of Cu, Cr, Co, Ni, Fe, and among these especially Raney catalysts and chromite catalysts. In addition to unsupported catalysts, supported catalysts are also used; more particularly, suitable support materials for Ru, Rh, Pd or Pt are activated carbon, alumina, $SiO_2$, $TiO_2$, $ZrO_2$ and silicates. The metal loading in the case of supported catalysts is typically in the range from 0.1 to 10% and preferably from 1 to 5% by weight. It has been found that Ru, Pd and Pt on activated carbon are particularly suitable.

The hydrogenation stage is performed continuously or batchwise in the presence of the acidic compound, which is present either dissolved in the aqueous solution, for example in the case of added inorganic or lower organic carboxylic acids, or which is present as a solid suspended in the aqueous solution, for example over fixed bed catalysts by the trickle mode or liquid phase mode, or else while stirring according to suspension hydrogenation.

In continuous mode, a catalyst hourly space velocity V/Vh, expressed in throughput volume per unit catalyst volume and unit time, of 0.1 to 1 $h^{-1}$, preferably of 0.2 to 0.5 $h^{-1}$, has been found to be appropriate. In the batchwise process regime, based on 100 parts by weight of aqueous starting solution neglecting the acidic compound, from 0.1 to 10 and preferably from 0.5 to 5 parts by weight of catalyst are used.

On completion of hydrogenation, the aqueous reaction mixture is freed of solids, for example by filtration, when hydrogenation has been effected in the presence of solid acidic compounds.

The hydrogenated material freed of solids is subsequently treated alternately with basic and acidic commercially available ion exchangers, the sequence of the treatment being of no importance. The hydrogenated material is first treated with an acidic ion exchanger, and the resulting eluate is then contacted with a basic ion exchanger, or vice versa. Customary temperatures in the range from 1 to 100° C., preferably in the range from 20 to 70° C., and standard pressure are employed. It has been found that the treatment with the ion exchangers is essential in order that ditrimethylolpropane is obtained with sufficient quality in the distillation residue in the subsequent distillative workup of the aqueous eluate. More particularly, the residual amounts of sulphate ash, determined to DIN 51575, modified with addition of sulphuric acid after the burning and before the annealing of the sample, in the remaining ditrimethylolpropane can be reduced significantly only by the treatment with the basic and acidic ion exchangers.

If the hydrogenation was effected in the presence of dissolved inorganic acids or lower organic carboxylic acids, the aqueous solution is neutralized by addition of base after removal of the hydrogenation catalyst. In this case too, there follows treatment with an acidic and basic ion exchanger, or vice versa, specifically at customary temperatures in the range from 1 to 100° C., preferably in the range from 20 to 70° C., and at standard pressure. The treatment with the ion exchangers removes not only the salts formed after addition of base but additionally further impurities which are responsible for increased occurrence of sulphate ash in the ditrimethylolpropane.

The basic ion exchangers include those which contain primary, secondary, tertiary or quaternary amino groups. Particular significance has been gained by polystyrene-based ion exchangers which contain tertiary amino groups or quaternary amino groups in the base form. Examples of weakly to strongly basic ion exchangers are Amberlit IR 45, Dowex 4 or Dowex Marathon-A. Particular industrial signfcance has been gained by macroreticular types such as Amberlyst A21, Lewatit MP62, Lewatit MP64, Imac A20, Zerolit G, Amberlit IRA93 or Amberlyst A26.

Weakly or strongly acidic ion exchangers contain, for example, the carboxylate group or the sulpho group, which are bonded to a polymer matrix based on styrene-divinylbenzene copolymers. The carboxylate group can be derived, for example, from aromatic carboxylic acids or aliphatic carboxylic acids, and the sulpho group from aromatic or aliphatic sulphonic acids. A strongly acidic ion exchanger is, for example, Amberlyst 15, Amberlyst DPT-1 or Dowex Marathon-C. The aqueous solution is contacted with the ion exchanger in a suitable reactor. The ion exchanger may be arranged, for example, as a fixed bed in a tubular reactor, through which the aqueous solution flows. The fixed bed volume and the size of the ion exchanger particles can be varied within wide ranges and thus adjusted to the selected reaction conditions and the process circumstances, such as the desired flow rate. It has been found to be useful to observe space velocities in the range from 1 to 10, especially from 5 to 8 ($V_{aqueous\ solution}/V_{ion\ exchanger}\cdot h$]). These are guide parameters which should appropriately be selected.

In another embodiment of the inventive procedure, the ion exchanger, which in this case may be very finely divided, is suspended in the aqueous solution. It is appropriate to keep the suspension in constant motion, for example by stirring or introducing a gas, for example air or nitrogen, in order to achieve intimate contact between the liquid phase and the ion exchanger. The mass ratio of liquid phase to ion exchanger can be adjusted substantially freely and hence in accordance with the individual requirements. It has been found to be useful, for every 100 parts by weight of aqueous solution, to use 1 to 10 and preferably 3 to 8 parts by weight of ion exchanger. For the performance of this process variant, stirred tanks or autoclaves, for example, are suitable. In this procedure, the ion exchanger, however, is subject to mechanical stress and, for the mixing of aqueous phase with the ion exchanger, the conditions should be adjusted such that abrasion at the surface of the particles or even mechanical damage to the particles is prevented.

The aqueous solution can be recirculated in order to complete the removal of impurities by multiple treatment of the aqueous phase. It is equally possible to perform the adsorption in several stages; either a batchwise or continuous reaction regime is possible.

After the treatment of the aqueous hydrogenation output with the basic and acidic ion exchangers, the resulting eluate is worked up by distillation. First, low boilers, especially water and methanol which has formed as a result of hydrogenation of the formaldehyde released in the acetal hydrolysis, are removed as first runnings. The low boilers are removed typically at bottom temperatures of 80 to 140° C. and at a slightly reduced pressure down to 500 hPa. After removal of the predominant amount of low boilers, the bottom temperature is increased to 180 to 230° C., and the pressure is simultaneously lowered down to 2 hPa. The top product obtained is a trimethylolpropane-enriched product stream with a content in the order of magnitude in the region of 90 to 96% by weight of trimethylolpropane. After predominant removal of the trimethylolpropane, the bottom temperature is raised up to 260° C. in order to drive out the last fractions of volatile components. Ditrimethylolpropane remains in the distillation residue as a pale yellowish liquid with a product of value content determined by gas chromatography in the range of 96 to 98% by weight in a quality sufficient for industrial applications and with a distinctly reduced sulphate ash content. After cooling to room temperature, a virtually white powder is obtained.

The trimethylolpropane-enriched product stream drawn off is recycled into the purifying stage of the overall process for the preparation of trimethylolpropane, appropriately into the purifying distillation stage to obtain trimethylolpropane. The pressure and temperature figures are guide values which can be optimized in a routine manner. In order to avoid the decomposition of the ditrimethylolpropane in the distillation bottoms, the bottom temperature, however, should not be increased too far above the guide values specified.

The distillative workup of the aqueous eluate from the treatment with the ion exchangers can be effected either batchwise or continuously. The distillation columns customary in industry are suitable, which appropriately have from 2 to 30 plates.

The process according to the invention permits the economic utilization of high-boiling fractions and residues which are obtained in the distillative purification of trimethylolpropane. The recycling of the trimethylolpropane-rich product streams obtained therefrom in the overall preparation process allows the plant efficiency to be improved and the yield of trimethylolpropane to be increased by about 3 to 7% compared to a process regime in which the high-boiling fractions and residues from the trimethylolpropane distillation are not worked up and not recycled. At the same time, the inventive procedure gives rise to ditrimethylolpropane as a distillation residue in a quality sufficient for industrial applications, without any need for an additional distillation of the ditrimethylolpropane, which can be performed only with very great difficulty, or complex recrystallization steps.

The examples which follow describe the process according to the invention in detail. It is of course not restricted to the embodiment described.

EXAMPLES

Example 1

For the inventive workup of the high-boiling fractions and residues from the distillative purification of trimethylolpropane, a mixture was used which had the following composition determined by gas chromatography (%):

| | |
|---|---|
| First runnings | 1.7 |
| Monocyclic formal (I) | 0.1 |
| Trimethylolpropane | 19.3 |
| Intermediate fraction I | 3.1 |
| Ditrimethylolpropane | 20.2 |
| Intermediate fraction II | 16.4 |
| Linear bistrimethylolpropane formal (II) | 32.7 |
| High boilers | 6.5 |

Water at 60° C. was added to the organic residue to produce a homogeneous aqueous solution with a content of 60% by weight of dissolved organic residue. To 100 parts by weight of aqueous solution were added 5 parts by weight of a commercial ruthenium-on-activated carbon catalyst in powder form with a metal loading of 5% by weight, and 2 parts by weight of an acidic commercial Y-type zeolite. The resulting suspension was subsequently treated with hydrogen in a 1 liter autoclave under the following conditions:

TABLE 1

Hydrogenation of an aqueous solution of residues from the trimethylolpropane distillation over ruthenium-on-activated carbon in the presence of Y-type zeolite

| Reaction conditions | Experiment 1 | Experiment 2 | Experiment 3 | Experiment 4 (comparative) |
|---|---|---|---|---|
| Temperature (° C.) | 200 | 200 | 200 | 130 |
| Pressure (MPa) | 4 | 8 | 20 | 20 |
| Reaction time (h) | 5 | 5 | 5 | 5 |
| Composition determined by gas chromatography (%; organic content, anhydrous): | | | | |
| First runnings | 5.2 | 4.7 | 1.6 | 1.1 |
| Monocycl. formal (I) | 0.2 | 0.1 | 0.6 | 20.2 |
| Trimethylolpropane | 74.4 | 72.7 | 76.4 | 56.6 |
| Intermediate fraction I | 4.2 | 1.4 | 1.5 | 5.3 |
| Ditrimethylolpropane | 15.5 | 20.8 | 19.6 | 16.3 |
| Intermediate fraction II | 0.1 | 0.1 | 0.1 | 0.2 |
| Linear bistrimethylolpropane formal (II) | 0.1 | 0.1 | 0.1 | 0.1 |
| High boilers | 0.3 | 0.1 | 0.1 | 0.2 |

Example 2

For the inventive workup of the high-boiling fractions and residues from the distillative purification of trimethylolpropane, a mixture was used which had the following composition determined by gas chromatography (%):

| | |
|---|---|
| First runnings | 0 |
| Monocyclic formal (I) | 0 |
| Trimethylolpropane | 7.0 |
| Intermediate fraction I | 19.8 |
| Ditrimethylolpropane | 20.3 |
| Intermediate fraction II | 0.1 |
| Linear bistrimethylolpropane formal (II) | 47.0 |
| High boilers | 5.8 |

Water at 60° C. was added to the organic residue to produce a homogeneous aqueous solution with a content of 60% by weight of dissolved organic residue. To 100 parts by weight of aqueous solution were added 0.5 part by weight of a commercial ruthenium-on-activated carbon catalyst in powder form with a metal loading of 5% by weight, and 0.5 part by weight of an acidic commercial Y-type zeolite. The resulting suspension was subsequently treated with hydrogen in a 1 liter autoclave under the following conditions:

TABLE 2

Hydrogenation of an aqueous solution of residues from trimethylolpropane distillation over ruthenium-on-activated carbon in the presence of Y-type zeolite

| Reaction conditions | Experiment 5 | Experiment 6 | Experiment 7 | Experiment 8 | Experiment 9 |
|---|---|---|---|---|---|
| Temperature (° C.) | 190 | 200 | 210 | 220 | 230 |
| Pressure (MPa) | 13 | 13 | 13 | 13 | 13 |
| Reaction time (h) | 3 | 3 | 3 | 3 | 3 |

TABLE 2-continued

Hydrogenation of an aqueous solution of residues from trimethylolpropane distillation over ruthenium-on-activated carbon in the presence of Y-type zeolite

| Reaction conditions | Experiment 5 | Experiment 6 | Experiment 7 | Experiment 8 | Experiment 9 |
|---|---|---|---|---|---|
| Composition determined by gas chromatography (%; organic content, anhydrous): | | | | | |
| First runnings | 4.3 | 5.2 | 6.3 | 5.9 | 8.9 |
| Monocycl. formal (I) | 8.9 | 3.9 | 1.9 | 0.2 | 0.2 |
| Trimethylolpropane | 60.9 | 65.1 | 65.7 | 68.1 | 64.7 |
| Intermediate fraction I | 3.7 | 2.3 | 1.9 | 1.6 | 1.6 |
| Ditrimethylolpropane | 21.7 | 23.1 | 23.8 | 23.9 | 24.2 |
| Intermediate fraction II | 0.1 | 0.1 | 0.1 | 0.1 | 0.1 |
| Linear bistrimethylolpropane formal (II) | 0.1 | 0.1 | 0.1 | 0.1 | 0.1 |
| High boilers | 0.3 | 0.2 | 0.2 | 0.1 | 0.2 |

After filtration of the catalyst and of the acidic zeolite, the aqueous solution obtained after hydrogenation, at a temperature of 20° C., was pumped first through a bed filled with the basic ion exchanger Dowex Marathon-A at a space velocity V/Vh of 5 h$^{-1}$, and then through a bed filled with the acidic ion exchanger Dowex Marathon-C, likewise with a space velocity V/Vh of 5 h$^{-1}$. The resulting eluate was subsequently distilled batchwise in a customary 20 cm Vigreux column. The course of the distillative workup and the gas chromatography analysis (%) of the individual fractions and of the distillation residue are compiled in Table 3 below.

The results of the continuously performed distillation of the resulting aqueous eluate are reproduced in Table 4. The bottom product of the first distillation was used as the starting material for the second distillation. For the distillations, laboratory columns randomly packed with Raschig rings were used with eight theoretical plates in the first distillation and with four theoretical plates in the second distillation.

TABLE 3

Batchwise distillative workup of the aqueous solution of residues from trimethylolpropane preparation after hydrogenation and treatment with ion exchangers

| | Input | 1st fraction | 2nd fraction | 3rd fraction | 4th fraction | 5th fraction | 6th fraction | Residue |
|---|---|---|---|---|---|---|---|---|
| Top temp. ° C. | | 98-104 | 20-24 | 132-173 | 178-190 | 210-220 | 220-224 | |
| Bottom temp. ° C. | | 100-180 | 70-160 | 176-190 | 196-240 | 250 | 250 | |
| Pressure hPa | | 1013 | 10 | 10 | 10 | 2 | 2 | |
| Weight (grams) * | 4662.4 | 1980.1 | 16.5 | 957.9 | 967.1 | 296.6 | 61.0 | 353.9 |
| % age | | 42.5 | 0.4 | 20.5 | 20.7 | 6.4 | 1.3 | 7.6 |
| Water content (%) | 40 | 95 | | | | | | |
| Gas chromatography analysis (%): | | | | | | | | |
| First runnings | 1.2 | 0.8 | 0 | 0 | 0 | 0 | 0 | 0 |
| Monocycl. formal (I) | 5.1 | 57.8 | 6.6 | 0.1 | 0.2 | 0.1 | 0.1 | 0.1 |
| Trimethylolpropane | 77.8 | 36.2 | 92.3 | 98.5 | 87.0 | 2.4 | 0.1 | |
| Intermediate fraction I | 1.0 | 5.2 | 0.9 | 0.5 | 3.5 | 6.2 | 0.4 | |
| Ditrimethylolpropane | 14.9 | 0 | 0.2 | 0.9 | 9.2 | 90.4 | 97.4 | |
| Intermediate fraction II | 0 | 0 | 0 | 0 | 0 | 0 | 0.1 | |
| Linear bistrimethylolpropane formal (II) | 0 | 0 | 0 | 0 | 0 | 0 | 0.1 | |
| High boilers | 0 | 0 | 0 | 0 | 0.1 | 0.9 | 1.8 | |

* Distillation loss: input (grams) − (sum of 1st-6th fraction + residue); corresponds to 29.3 grams (0.6%)

TABLE 4

Continuous distillative workup of the aqueous solution of residues from trimethylolpropane preparation after hydrogenation and treatment with ion exchangers

| | | Input | Distillation 1 8 plates Tops | Bottoms Distillation 1 | Distillation 2 4 plates Bottoms Distillation 2 |
|---|---|---|---|---|---|
| Pressure | [hPa] | | 10 | | 2 |
| Top | [° C.] | | 156-198 | | 204 |
| Bottom | [° C.] | | 185-240 | | 261 |
| Return ratio | | | none | | none |
| Amount [g/h]* | | 1711.5 | 1221.6 | 486.6 | 432.6 |

TABLE 4-continued

Continuous distillative workup of the aqueous solution of residues from trimethylolpropane preparation after hydrogenation and treatment with ion exchangers

|  | Input | Distillation 1 8 plates Tops | Bottoms Distillation 1 | Distillation 2 4 plates Bottoms Distillation 2 |
|---|---|---|---|---|
| Gas chromatography analysis (%): | | | | |
| First runnings | 1.1 | 2.1 | 0 | 0 |
| Monocycl. Formal (I) | 8.2 | 11.6 | 0 | 0 |
| Trimethylolpropane | 61.9 | 83.4 | 0.8 | 0.1 |
| Intermediate fraction I | 3.5 | 2.8 | 8.7 | 0.9 |
| Ditrimethylolpropane | 25.0 | 0 | 87.7 | 96.7 |
| Intermediate fraction II | 0.1 | 0.1 | 0.5 | 0 |
| Linear bistrimethylolpropane formal (II) | 0 | 0 | 0 | 0 |
| High boiler | 0.2 | 0 | 2.3 | 2.3 |

*Mass balance [g/h]:
First distillation: Input: 1711.5 Bottoms: 486.6 Tops: 1221.6 Distillation loss: 3.3
Second distillation: Input: 486.6 Bottoms: 432.6 Tops/Distillation loss: 54.0

The resulting distillation residue of ditrimethylol-propane was subsequently analyzed for the sulphate ash content to DIN 51575, modified with addition of sulphuric acid. The ditrimethylolpropane residues obtained by the process according to the invention had a sulphate ash content in the range from 200 to 300 ppm.

Comparative Example

The hydrogenation of the aqueous solution of residues from the trimethylolpropane distillation was undertaken analogously to Examples 1 to 3. In contrast to the inventive procedure, subsequent to removal of solids, the aqueous solution was fractionally distilled without treatment with the acidic and basic ion exchangers. The sulphate ash content was determined in the resulting ditrimethylolpropane residues, likewise by the modified process according to DIN 51575. Without the treatment of the aqueous hydrogenation output with ion exchangers, sulphate ash contents of 1000 to 1500 ppm were detected.

As the inventive examples demonstrate, a trimethylol-propane-rich product stream can be removed by distillation from the high-boiling fractions and residues which are obtained in the distillative purification of trimethylolpropane, while, at the same time, ditrimethylolpropane with a reduced sulphate ash content which is of sufficient quality for industrial applications remains in the distillation residue.

The invention claimed is:

1. Process for obtaining ditrimethylolpropane and trimethylolpropane-enriched product streams from the high-boiling fractions and residues which are obtained in the distillative purification of trimethylolpropane, characterized in that:
   (a) these high-boiling fractions and residues are combined and water is added to produce an aqueous solution;
   (b) the aqueous solution produced according to step a) is treated at a temperature of 160 to 280° C. and at a pressure of 1 to 30 MPa with hydrogen in the presence of a catalyst and of an acidic compound;
   (c) the aqueous solution obtained according to step b) is removed from the catalyst and further solids, if present;
   (d) the aqueous solution obtained according to step c) is treated both with basic and with acidic ion exchangers;
   (e) water and low boilers present are removed from the aqueous eluate obtained according to step d); and
   (f) a trimethylolpropane-enriched product stream is distilled out of the residue obtained after step e) at elevated temperature and reduced pressure, leaving ditrimethylolpropane as the distillation residue.

2. Process according to claim 1, characterized in that the aqueous solution according to step a) is produced at a temperature of more than 50° C.

3. Process according to claim 1, characterized in that the treatment of the aqueous solution in step b) with hydrogen is effected at a temperature of 180 to 230° C. and at a pressure in the range from 6 to 20 MPa.

4. Process according to claim 1, characterized in that the acidic compound present in step b) is selected from the group of protic inorganic acids, organic acids and acidic solids.

5. Process according to claim 4, characterized in that the protic inorganic acids used are phosphoric acid or sulphuric acid.

6. Process according to claim 4, characterized in that the organic acids used are formic acid, acetic acid, propionic acid or the isomeric butyric acids.

7. Process according to claim 4, characterized in that the acidic solids used are acidic alumina, acidic zeolites or acidic ion exchangers.

8. Process according to claim 1, characterized in that the catalyst used in step b) is a hydrogenation catalyst comprising a noble metal from the group of Ru, Rh, Pd and Pt, or comprising Co and Ni.

9. Process according to claim 8, characterized in that the hydrogenation catalyst comprises activated carbon, alumina, $SiO_2$, $TiO_2$, $ZrO_2$ or silicates as support material.

10. Process according to claim 1, characterized in that, in step f), a trimethylolpropane-enriched product stream is distilled out of the residue at a temperature of up to 260° C.

11. Process for obtaining ditrimethylolpropane and trimethylolpropane-enriched product streams from the high-boiling fractions and residues which are obtained in the distillative purification of trimethylolpropane, characterized in that:
   (a) these high-boiling fractions and residues are combined and water is added to produce an aqueous solution;
   (b) the aqueous solution produced according to step a) is treated at a temperature of 160 to 280° C. and at a pressure of 1 to 30 MPa with hydrogen in the presence of a hydrogenation catalyst comprising a noble metal selected from the group of Ru, Rh, Pd and Pt, or comprising Co and Ni and in the presence of an acidic compound selected from the group of protic inorganic acids, organic acids and acidic solids;
(c) the aqueous solution obtained according to step b) is removed from the catalyst and further solids, if present;
(d) the aqueous solution obtained according to step c) is treated both with basic and with acidic ion exchangers;
(e) water and low boilers present are removed from the aqueous eluate obtained according to step d); and
(f) a trimethylolpropane-enriched product stream is distilled out of the residue obtained after step e) at elevated temperature and reduced pressure, leaving ditrimethylolpropane as the distillation residue.

12. Process according to claim 11, characterized in that the protic inorganic acids used are phosphoric acid or sulphuric acid.

13. Process according to claim 11, characterized in that the organic acids used are formic acid, acetic acid, propionic acid or the isomeric butyric acids.

14. Process according to claim 11, characterized in that the acidic solids used are acidic alumina, acidic zeolites or acidic ion exchangers.

15. Process according to claim 11, characterized in that the hydrogenation catalyst comprises activated carbon, alumina, $SiO_2$, $TiO_2$, $ZrO_2$ or silicates as support material.

* * * * *